United States Patent
Maguire, Jr. et al.

(10) Patent No.: US 8,557,365 B2
(45) Date of Patent: Oct. 15, 2013

(54) STERILIZATION ACCESSORY FORMED FROM OPEN CELLULAR MATERIAL

(75) Inventors: Walter L. Maguire, Jr., Guilford, CT (US); Shaun Sweeney, Hamburg, NJ (US)

(73) Assignee: Cygnus Medical, LLC, Branford, CT (US)

( * ) Notice: Subject to any disclaimer, the term of this patent is extended or adjusted under 35 U.S.C. 154(b) by 706 days.

(21) Appl. No.: 11/414,398

(22) Filed: Apr. 28, 2006

(65) Prior Publication Data

US 2007/0253864 A1 Nov. 1, 2007

(51) Int. Cl.
| | |
|---|---|
| *B32B 3/10* | (2006.01) |
| *A61L 2/00* | (2006.01) |
| *A61L 9/00* | (2006.01) |
| *B65D 83/10* | (2006.01) |
| *B65D 81/02* | (2006.01) |
| *B65D 85/00* | (2006.01) |

(52) U.S. Cl.
USPC ........... 428/131; 422/292; 422/295; 422/297; 422/300; 206/370; 206/523; 428/137

(58) Field of Classification Search
USPC ........ 422/300, 292, 297, 22, 23, 28; 206/363, 206/370, 439, 440, 523; 428/158, 159, 156, 428/213, 220, 131, 137
See application file for complete search history.

(56) References Cited

U.S. PATENT DOCUMENTS

| | | | | |
|---|---|---|---|---|
| 4,196,245 A | * | 4/1980 | Kitson et al. | 428/198 |
| 4,550,546 A | * | 11/1985 | Raley et al. | 53/425 |
| 5,698,294 A | * | 12/1997 | Van Hout et al. | 428/156 |
| 5,749,111 A | * | 5/1998 | Pearce | 5/652 |
| 6,210,638 B1 | * | 4/2001 | Grieco et al. | 422/22 |
| 6,248,293 B1 | | 6/2001 | Davis et al. | 422/28 |
| 6,391,260 B1 | | 5/2002 | Davis et al. | 422/28 |
| 6,440,375 B1 | | 8/2002 | Davis et al. | 422/300 |
| 6,902,712 B2 | | 6/2005 | Davis | 422/300 |
| 2002/0064478 A1 | * | 5/2002 | Davis | 422/26 |
| 2005/0016886 A1 | * | 1/2005 | Riley | 206/438 |
| 2005/0163686 A1 | * | 7/2005 | Bettenhausen et al. | 422/292 |
| 2007/0095699 A1 | * | 5/2007 | Frieze et al. | 206/438 |

* cited by examiner

*Primary Examiner* — Regina M Yoo
(74) *Attorney, Agent, or Firm* — St. Onge Steward Johnston & Reens LLC

(57) ABSTRACT

A sterilization system for sterilizing a surgical instrument includes a generally planar sterilization surface and a sterilization accessory disposed on the sterilization surface. The sterilization accessory is adapted to receive the surgical instrument thereon or therein, and the sterilization accessory is formed at least in part from an open cellular material. The open cellular material includes a generally planar base surface, a plurality of cells extending from the base surface, each of the plurality of cells including a side wall, which extends from the base surface, and an end wall. Each of the plurality of cells is open, such that gases surrounding the open cellular material are free to pass into and out of each of the plurality of cells.

11 Claims, 5 Drawing Sheets

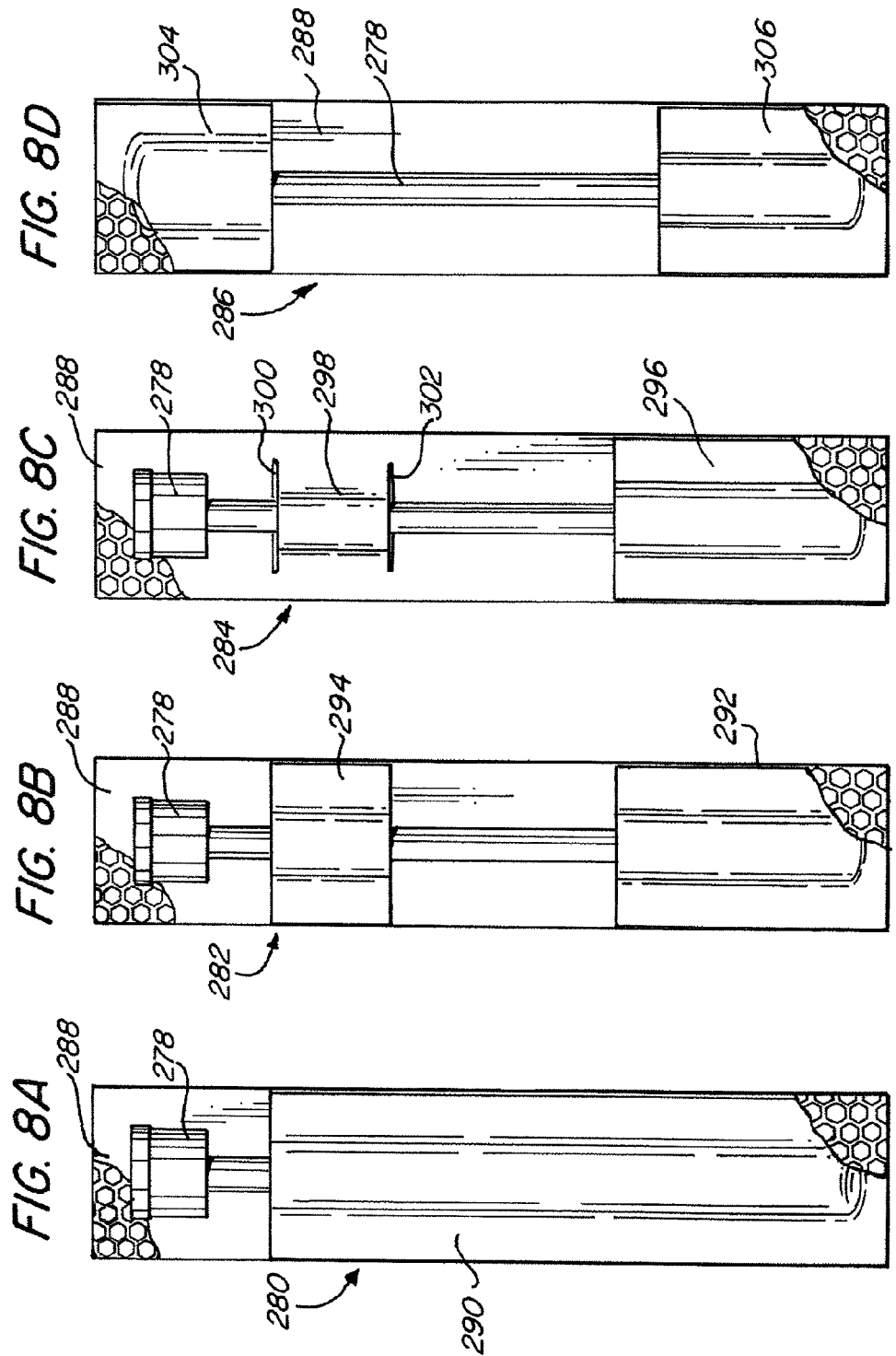

STERILIZATION ACCESSORY FORMED FROM OPEN CELLULAR MATERIAL

FIELD OF THE INVENTION

The present invention relates generally to apparatus and methods for protecting instruments and the like during sterilization processes, and more particularly to liners, such as trayliners and shelf-liners, and instrument pouches for protecting articles, such as surgical instruments, for use in sterilization processes.

BACKGROUND OF THE INVENTION

As is well known, surgical instruments used in the healthcare industry must be sterilized before and after each use. Sterilization, of course, frees instruments from microorganism contamination, to prevent infections and the spread of diseases among patients. All medical procedures rely upon a stringent program of sterilization.

The medical device industry has addressed the sterilization requirements in the surgical field by offering two general types of surgical instruments: reusable instruments and single use, or disposable, instruments. Reusable instruments are typically composed of stainless steel and are typically sterilized before their initial use and then cleaned and resterilized prior to each subsequent use thereof. Single use or disposable instruments, on the other hand, are often fabricated primarily from plastic materials, thereby reducing costs associated with manufacture, and are discarded after use in a single procedure.

With respect to reusable surgical instruments, e.g., forceps, graspers, dissectors, probes, hemostats, scissors and the like, sterilization and resterilization had historically been accomplished using two primary sterilization modalities: steam sterilization and ethylene oxide sterilization. Of these two primary historical sterilization modalities, steam sterilization had traditionally been the overwhelmingly dominant method of sterilization in the surgical instrument field.

In a broad sense, these historical sterilization processes generally involved placing instruments to be sterilized in a tray, wrapping the instruments and the tray with a sterilization wrap, and placing the wrapped tray and instruments in a sterilization chamber, where the instruments were exposed to the sterilization medium of either steam or ethylene oxide. The instruments were preferably placed in a tray and wrapped before initiating exposure to the sterilization medium. Wrapping the tray generally contributed to providing a level of protection to the surgical instruments, e.g., during post-sterilization storage and handling prior to actual use, and to maintaining the instruments in a dry, sterile condition. Typically, sterilization trays were wrapped with a sterilization wrap, e.g., paper. Other instruments to be sterilized include basins. Basins were separated by cotton towels or other absorbent materials and then wrapped in sterilization wrap prior to sterilization.

One long and continuing problem encountered with steam and ethylene oxide sterilization, however, is the presence of moisture that remains on the implements such as on sterilized instruments, i.e., within the sterile wrap, at the conclusion of the sterilization process. This residual moisture can range from slight levels of dampness to visible droplets on the surface of surgical instruments. Such residual moisture is both undesirable and is unacceptable because such moisture could permit migration of surface microorganisms, thereby penetrating the wrapped tray or basin and rendering its contents contaminated.

A wrapped tray or basin with residual moisture has been termed a "wet pack," i.e., a wrapped tray containing surgical instruments having surface moisture on the inside and/or outside of the wrapped tray, e.g., during and after the sterilization process. Wet pack problems may be caused and/or exacerbated by, e.g., the use of new sterilizers, boiler or plumbing changes or even ambient humidity variations due to air conditioning, etc.

Another problem associated with steam and ethylene oxide sterilization arises when the wrapped trays and basins are loaded on sterilization carts having multiple shelves and rails and which are then wheeled into a sterilizer where the wrapped trays are sterilized along with the cart. In such a case, condensation may drip from a shelf or a rail onto the wrapped tray causing a wet pack. Also, the wrapped tray or basin may become stained during sterilization or even torn during loading or removal from a sterilization cart because of the condition of the sterilization cart. That is because during repeated use, the sterilization carts may begin to oxidize and degrade, exposing sharp edges.

In some cases, shelves of sterilization carts may be laboriously wrapped with absorbent wrappers or thermal blankets that then must be adhered to the shelves. In a further step, the edges of the absorbent wrappers or thermal blankets must also be bound to prevent fraying and shedding of the wrappers or blankets and subsequent passage thereof into the sterilization medium. Since the absorbent wrappers and thermal blankets require a large amount of labor to replace, the sterilization carts generally undergo an excessively high number of sterilization cycles in the sterilizer before they are replaced. This allows for the buildup of undesirable materials and microorganisms within the absorbent wrappers and thermal blankets.

Many of the disadvantages associated with the two primary sterilization modalities historically used, which are discussed above, are obviated by a third sterilization technique, low temperature hydrogen-peroxide gas plasma sterilization, which is now also being commonly used. For a number of well-known reasons, hydrogen-peroxide gas plasma sterilization is becoming a popular sterilization method. For example, hydrogen-peroxide gas plasma sterilization has significantly less corrosive effect on metal surgical instruments, and leaves no residue that may cause the sterilized surgical instruments to be irritating or toxic to patients. In addition, hydrogen-peroxide gas plasma sterilization produces no toxic byproducts and requires no special ventilation or aeration. Hydrogen-peroxide gas plasma sterilization is also faster than other sterilization processes since a waiting period to allow toxic byproducts to dissipate is unnecessary.

A STERRAD® hydrogen-peroxide gas plasma sterilization system available from Advanced Sterilization Products of Irvine, Calif., for example, is designed to provide non-toxic, dry, low-temperature sterilization in about one hour, without toxic residues. However, the STERRAD® system is not usable with cellulose-based products like linen or paper normally used in other sterilization processes. Cellulose-based products, as well as many other materials commonly used in sterilization, are highly absorbent and trap fluid during the sterilization process. This is highly undesirable in hydrogen-peroxide gas plasma sterilization.

During hydrogen-peroxide gas plasma sterilization, a vacuum is created within the sterilization chamber and a small amount of hydrogen peroxide (e.g., 1 Tbsp) is introduced therein, which, due to the vacuum, vaporizes and substantially fills the chamber. An electrical current is then passed through the chamber in order to convert the vaporized hydrogen peroxide into plasma. As should be obvious to those skilled in the art, any absorbent materials (such as tray liners, pouches, etc.) within the sterilization chamber can trap the hydrogen peroxide vapors, thereby preventing such vapors from filling the chamber and preventing a sufficient amount of plasma from being created.

A similar problem exists with open-cell urethane-based (e.g., polyurethane) foam products, which have been sometimes used in connection with sterilization processes. More specifically, it has been found that the hydrogen peroxide used in connection with hydrogen-peroxide gas plasma sterilization can chemically react with such open-cell urethane-based foam products, such that there is no longer enough vaporized hydrogen peroxide to create sufficient plasma during sterilization.

The STERRAD® system includes a sterilization chamber and a tray for holding surgical instruments and articles such as fiber optic endoscopes, laser handpieces, power drills and ophthalmic devices, within the sterilization chamber during the sterilization process. The tray includes a base having a multiplicity of holes for allowing plasma to flow there through and contact the article being sterilized during the sterilization process.

Existing trayliners and instrument protective pouches for use with the STERRAD® system are known. Examples of such products are available from Cygnus Medical, assignee of the present application, under the trademark Plasma-Cel™. These known trayliners and pouches are formed of an open-cell polyethylene foam, which allows plasma to pass directly through the trayliner or pouch, such that the foam structures do not interfere with the passage of plasma through the tray holes. While these particular open cell foam structures have been found to work effectively with the STERRAD® system, since open cell polyethylene (as well as other open cell foams) is relatively expensive, the structures formed from these materials typically must be reused a number of times to make each individual trayliner or pouch cost effective. Some users, however, feel comfortable with the idea of reusing, and keeping track of the number of uses of, a sterilization trayliner or pouch in a sterile hospital environment. Thus, the relatively expensive open cell polyethylene foam structures are often disposed of after a single use.

U.S. Pat. No. 6,902,712 discloses a highly absorbent liner that may be placed, in one embodiment, as a trayliner in a sterilization tray, e.g., along the tray bottom, or, in another embodiment as a shelf-liner, on a shelf of a sterilization cart, to absorb potential residual moisture generated during the sterilization process. The liner is fabricated from a hydrophilic polyurethane foam.

However, as discussed above, it is undesirable in connection with certain types of sterilization techniques (e.g., hydrogen-peroxide gas plasma sterilization) for absorbent materials to be employed. For example, during hydrogen-peroxide gas plasma sterilization, the highly absorbent material disclosed in U.S. Pat. No. 6,902,712 may cause a significant portion of the hydrogen peroxide to be trapped, such that sufficient amounts of plasma are not created. This problem may be compounded by chemical reaction between the hydrophilic polyurethane foam and the hydrogen peroxide, as described above. Moreover, also as discussed above, the hydrophilic polyurethane foam disclosed in U.S. Pat. No. 6,902,712 is relatively expensive, and the structures formed from these materials typically must be reused a number of times to make each individual trayliner or pouch cost effective.

U.S. Pat. No. 6,391,260 discloses instrument pouches particularly adapted for use in connection with hydrogen-peroxide gas plasma sterilization units. More specifically, an instrument is placed within an instrument pouch in accordance with the invention, and the instrument pouch containing the article is placed within the sterilization chamber of the sterilization unit. The hydrogen-peroxide gas plasma sterilization unit is then operated such that the instrument within the instrument pouch is sterilized, whereby the instrument pouch containing the article is removed from the sterilization unit. The sterilized instrument is left within the instrument pouch until the sterilized instrument is actually used. The instrument pouch is fabricated from a closed cell foam plastic material.

However, while pouches formed from a closed cell foam plastic material may be appropriate for use in connection with hydrogen-peroxide gas plasma sterilization, pouches formed from this material may not provide an adequate level of protection (i.e., cushioning) for the surgical instruments, and may not be cost effective.

What is desired, therefore, is a sterilization accessory which is formed of a material that is capable of being used in conjunction with hydrogen-peroxide gas plasma sterilization, which is formed of a material that does not undesirably trap significant amounts of hydrogen peroxide therein so as to reduce the effectiveness of the sterilization operation, which is formed of a material that does not undesirably chemically react with hydrogen peroxide so as to reduce the effectiveness of the sterilization operation, and which is relatively inexpensive to produce, thereby making it cost effective to dispose of each accessory after a single use.

SUMMARY OF THE INVENTION

Accordingly, it is an object of the present invention to provide a sterilization accessory which is formed of a material that is capable of being used in conjunction with hydrogen-peroxide gas plasma sterilization.

Another object of the present invention is to provide a sterilization accessory having the above characteristics and which is formed of a material that does not undesirably trap significant amounts of hydrogen peroxide therein so as to reduce the effectiveness of the sterilization operation.

A further object of the present invention is to provide a sterilization accessory having the above characteristics and which is formed of a material that does not undesirably chemically react with hydrogen peroxide so as to reduce the effectiveness of the sterilization operation.

Still another object of the present invention is to provide a sterilization accessory having the above characteristics and which is relatively inexpensive to produce, thereby making it cost effective to dispose of each accessory after a single use.

These and other objects of the present invention are achieved in accordance with one embodiment of the present invention by provision of a sterilization system for sterilizing a surgical instrument, the sterilization system including a generally planar sterilization surface, and a sterilization accessory disposed on the sterilization surface. The sterilization accessory is adapted to receive the surgical instrument thereon or therein, and the sterilization accessory is formed at least in part from an open cellular material. The open cellular material includes a generally planar base surface, a plurality of cells extending from the base surface, each of the plurality of cells including a side wall, which extends from the base surface, and an end wall. Each of the plurality of cells is open, such that gases surrounding the open cellular material are free to pass into and out of each of the plurality of cells.

In some embodiments, the side wall of each of the plurality of cells extends from the base surface at an angle oblique with respect thereto. In some embodiments, the end wall is discrete from the side wall of each of the plurality of cells, such that a clear demarcation therebetween is readily ascertainable. In some embodiments, the end wall is integrally formed with the side wall of each of the plurality of cells, such that a clear demarcation therebetween is not readily ascertainable.

In some embodiments, each of the plurality of cells has formed in the end wall or the side wall thereof, an aperture, which aperture permits gases surrounding the open cellular material to pass into and out of each of the plurality of cells. In certain of these embodiments, the open cellular material further comprises a substantially planar sheet of material provided adjacent the base surface. In certain of these embodiments, the sheet of material is sealed to the base surface along an entire perimeter of each of the plurality of cells, such that substantially the only means for gases to enter and escape from the plurality of cells is through the apertures. In certain embodiments, the sheet of material is sealed to the base surface along only a portion of a perimeter of each of the plurality of cells, such that each of the plurality of cells is in fluid communication with adjacent ones of the plurality of cells through openings between the sheet of material and the base surface.

In some embodiments, each of the plurality of cells has a hexagonal cross section. In some embodiments, the generally planar sterilization surface comprises a sterilization tray. In some embodiments, the generally planar sterilization surface comprises a shelf of a sterilization cart. In some embodiments, the sterilization accessory comprises a trayliner or shelf liner. In some embodiments, the sterilization accessory comprises an instrument pouch. In some embodiments, the sterilization accessory is formed from an olefin-based material. In certain of these embodiments, the sterilization accessory is formed from at least one of polyethylene and polypropylene.

In accordance with another embodiment of the present invention, a sterilization accessory, adapted to receive a surgical instrument thereon or therein during sterilization thereof, is formed at least in part from an open cellular material which includes a plurality of cells. Each of the plurality of cells includes a side wall and an end wall, with the side wall and the end wall which form a part of each of the plurality of cells being each associated with only a single one of the plurality of cells, and not being shared with any other of the plurality of cells. Each of the plurality of cells is open, such that gases surrounding the open cellular material are free to pass into and out of each of the plurality of cells.

In some embodiments, the open cellular material further comprises a generally planar base surface from which extends the side wall of each of the plurality of cells. In certain of these embodiments, the side wall of each of the plurality of cells extends from the base surface at an angle oblique with respect thereto. In some embodiments, the end wall is discrete from the side wall of each of the plurality of cells, such that a clear demarcation therebetween is readily ascertainable. In some embodiments, the end wall is integrally formed with the side wall of each of the plurality of cells, such that a clear demarcation therebetween is not readily ascertainable.

In some embodiments, each of the plurality of cells has formed in the end wall or the side wall thereof, an aperture, which aperture permits gases surrounding the open cellular material to pass into and out of each of the plurality of cells. In certain of these embodiments, the open cellular material further comprises a generally planar base surface from which extends the side wall of each of the plurality of cells, and the open cellular material further comprises a substantially planar sheet of material provided adjacent the base surface. In certain of these embodiments, the sheet of material is sealed to the base surface along an entire perimeter of each of the plurality of cells, such that substantially the only means for gases to enter and escape from the plurality of cells is through the apertures. In certain embodiments, the sheet of material is sealed to the base surface along only a portion of a perimeter of each of the plurality of cells, such that each of the plurality of cells is in fluid communication with adjacent ones of the plurality of cells through openings between the sheet of material and the base surface.

In some embodiments, each of the plurality of cells has a hexagonal cross section. In some embodiments, the sterilization accessory comprises a trayliner or shelf liner. In some embodiments, the sterilization accessory comprises an instrument pouch. In some embodiments, the sterilization accessory is formed from an olefin-based material. In certain of these embodiments, the sterilization accessory is formed from at least one of polyethylene and polypropylene.

In accordance with another aspect of the present invention, a method for sterilizing an article in a sterilization chamber of a hydrogen-peroxide gas plasma sterilization unit is provided. The article is placed on or within a sterilization accessory formed at least in part from an open cellular material comprising a generally planar base surface, a plurality of cells extending from the base surface, each of the plurality of cells comprising a side wall, which extends from the base surface, and an end wall. Each of the plurality of cells is open, such that gases surrounding the open cellular material are free to pass into and out of each of the plurality of cells. The article and the sterilization accessory are placed within the sterilization chamber of the sterilization unit, and the sterilization unit is operated such that the article is sterilized.

In some embodiments, the operating step comprises the steps of introducing hydrogen peroxide into the sterilization chamber of the sterilization unit, vaporizing the hydrogen peroxide within the sterilization chamber of the sterilization unit, and passing an electrical current through the sterilization chamber of the sterilization unit in order create a plasma from the vaporized hydrogen peroxide. In certain of these embodiments, the vaporizing step comprises the steps of creating a vacuum within the sterilization chamber of the sterilization unit.

The invention and its particular features and advantages will become more apparent from the following detailed description considered with reference to the accompanying drawings.

BRIEF DESCRIPTION OF THE DRAWINGS

FIGS. 8A-8D are front views of various instrument pouches formed from the open cellular material of FIG. 1, with each pouch holding an ophthalmic device.

DETAILED DESCRIPTION OF AN EMBODIMENT OF THE INVENTION

Figure 1:
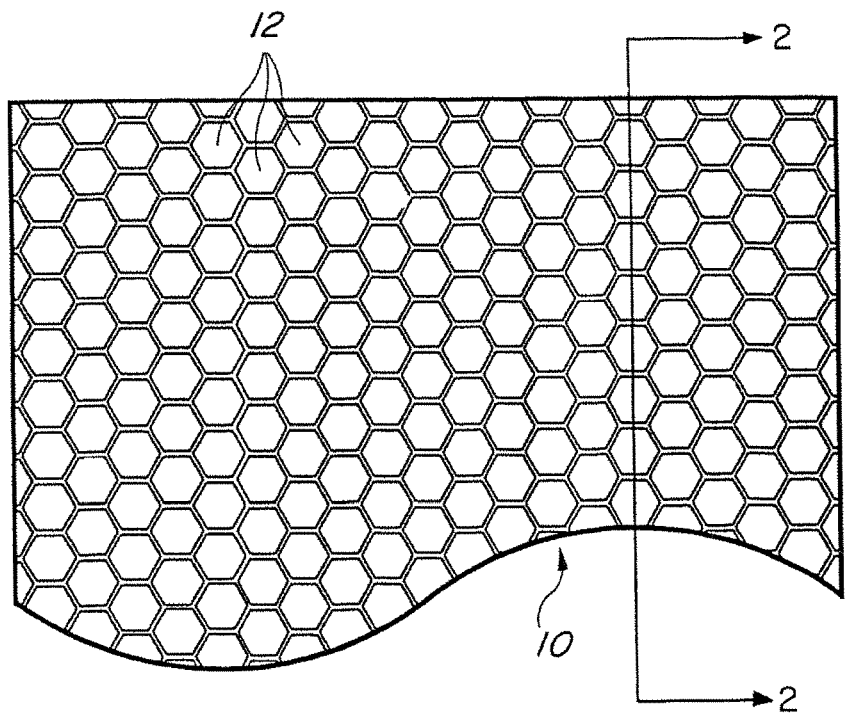
FIG. 1 is a top plan view of a portion of open cellular material of which a sterilization accessory in accordance with the present invention is formed.
Figure 2A:
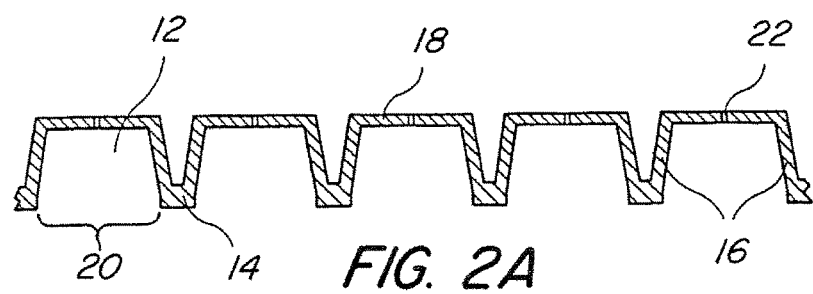
FIG. 2A is an enlarged, partially cross-sectional view of an embodiment of the open cellular material of FIG. 1, taken along line 2-2 of FIG. 1.
Figure 2B:
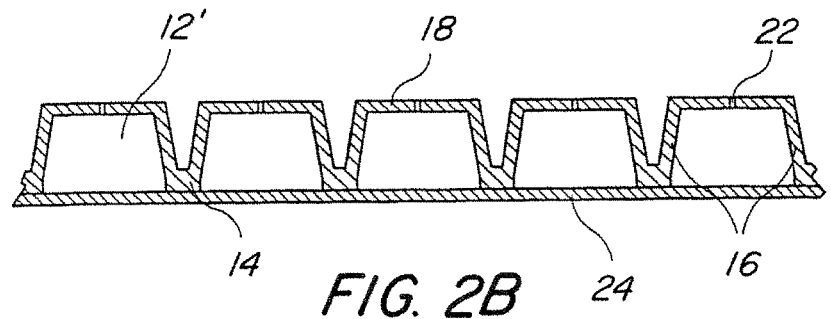
FIG. 2B is an enlarged, partially cross-sectional view of another embodiment of the open cellular material of FIG. 1, taken along line 2-2 of FIG. 1.

Referring first to FIGS. 1, 2A and 2B, a portion of open cellular material 10 of which a sterilization accessory in accordance with the present invention is formed is shown. Material 10 is generally a sheet material having formed therein a multiplicity of adjacent discrete cells 12. Although cells 12 are shown in FIG. 1 as being hexagonal, it should be understood that cells 12 may have any of a number of other shapes, such as being square, circular, rectangular, ovoid, pentagonal, octagonal, etc., in cross section. Preferably, although not necessarily, all of cells 12 have the same cross-sectional shape.

Referring now specifically to FIG. 2A, material 10 has a generally planar base surface 14 defined between cells 12, from which extend the side walls 16 of each of cells 12. Preferably, side walls 16 are tapered, that is, they extend from generally planar base surface 14 at an angle oblique thereto. Each of cells 12 also includes an end wall 18 extending between side walls 16. End wall 18 may be generally planar, as shown in FIG. 2A, or end wall 18 may be curved, undulating, etc. Moreover, end wall 18 may be discrete from side walls 16, such that a clear demarcation therebetween is readily ascertainable, such as is shown in FIG. 2A, or end wall 18 and side walls 16 may be formed together. For example, end wall 18 and side walls 16 may together define a dome-shaped, or generally dome-shaped configuration.

Opposite to end walls 18, each of cells 12 has an open end 20 which allows air within cells 12 to escape when material 10 is crushed. In addition, each of cells 12 preferably has formed therein, in end wall 18 and/or side walls 16, at least one aperture 22, which aperture allows air within cells 12 to escape, even if open end 20 is closed, for example, when material 10 is placed with its base surface 14 against a tray or some other planar surface which would close open end 20, thereby inhibiting air from escaping from cells 12.

As shown in FIG. 2A, base surface 14 may be formed so as to have a greater thickness than do side walls 16 and end wall 18. This may be desirable in some circumstances, as such may help material 10 to retain a generally planar configuration. As will be understood by those skilled in the art, such a configuration may be created, for example, by providing a generally planar sheet of material having uniform thickness, and then thermoforming or vacuum forming cells 12 into the sheet. Material 10 may be formed from polyethylene or other similar material.

Referring now to FIG. 2B, cells 12' are similar to cells 12 shown in FIG. 2A, with the exception that rather than open ends 20 being provided, a substantially planar sheet of material 24 is provided adjacent base surface 14. If desired, sheet of material 24 may be sealed to base surface 14 along the entire perimeters of each of cells 12'. When such is the case, substantially the only means for air to enter and escape from cells 12' would be through apertures 22. However, it may be desirable for sheet of material 24 may be sealed to base surface 14 along only a portion of the perimeters of each of cells 12', such that each of cells 12' is in fluid communication with adjacent cells 12' through openings between sheet of material 24 and base surface 14.

Material 10, with its multiplicity of open cells 12, 12', possesses a number of desirable properties which make it a preferred choice for forming sterilization accessories, such as trayliners, shelf liners, pouches, and the like. More specifically, the open cellular structure of material 10 enables it to safely conform to and provide superior cushioning protection for fragile items. Moreover, material 10 can be easily formed from base resins that are FDA approved and non-reactive in a sterilization environment. Material 10 is preferably formed from an olefin-based material, which materials are generally not chemically reactive with hydrogen peroxide, and is most preferably formed from polyethylene and/or polypropylene.

The tapered cell walls of material 10 absorb shock and dampen vibration, while cellular "memory" continuously delivers long-lasting high performance. The cushioning performance of material 10, unlike traditional "bubble wrap" is unaffected by punctures, age, temperature or atmospheric conditions, which means the cells will not and do not "pop," which would degrade cushioning performance.

While material 10 is specifically intended for use in connection with hydrogen-peroxide gas plasma sterilization, material 10 may also be used in connection with other sterilization techniques, such as ethylene oxide sterilization.

Figure 3:
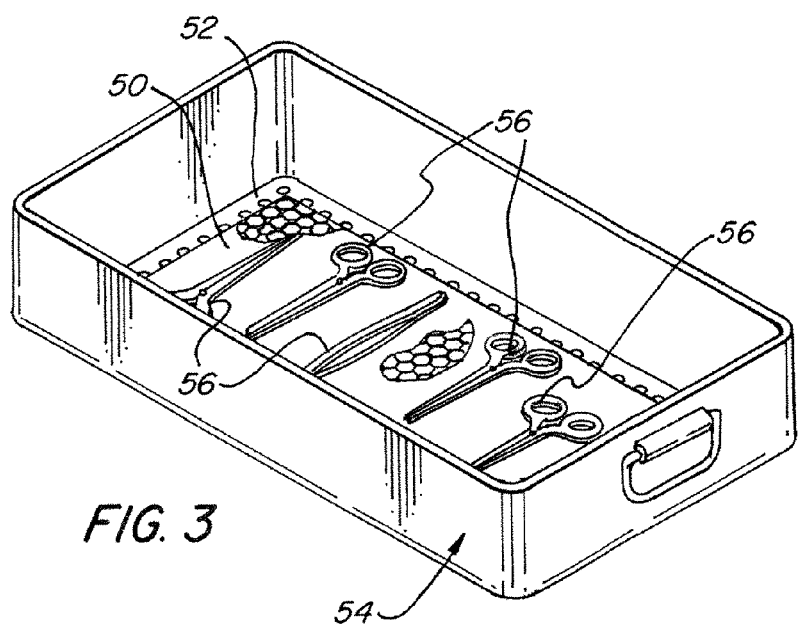
FIG. 3 is a perspective view of a trayliner formed from the open cellular material of FIG. 1, lying beneath surgical instruments and within a sterilization tray.
Figure 4:
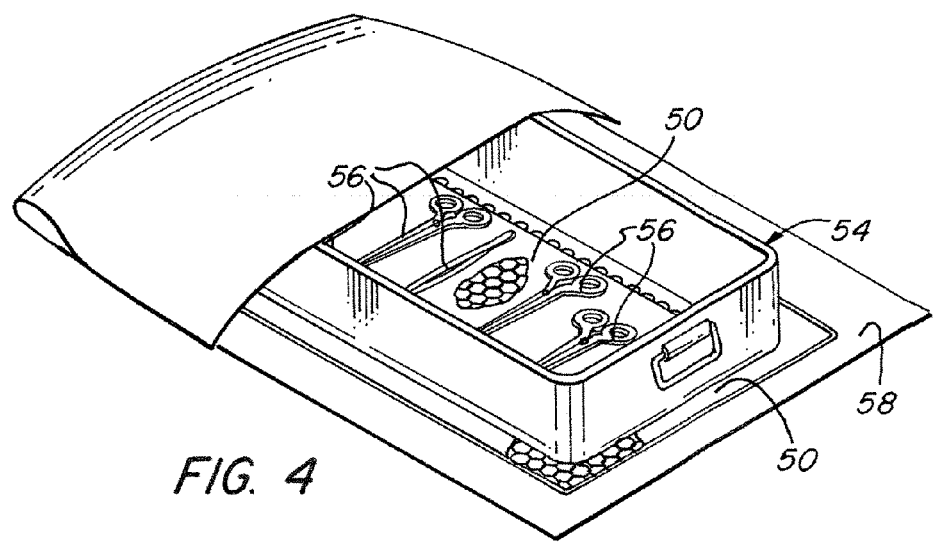
FIG. 4 is a perspective view of another trayliner formed from the open cellular material of FIG. 1, positioned under a sterilization tray with a sterilization wrap positioned therearound.

Referring now to FIGS. 3 and 4, a first embodiment of a sterilization accessory in accordance with the present invention is illustrated. In particular, a trayliner 50 is provided for introduction into a sterilizing system in connection with the sterilization process. The trayliner 50 of the present embodiment advantageously functions so as not to interfere with the creation of plasma during hydrogen-peroxide gas plasma sterilization, and further advantageously cushions surgical instruments to be sterilized, e.g., forceps, graspers, dissectors, probes, hemostats, scissors and the like, both during and after a sterilization process. Trayliner 50 is fabricated from the open cellular material 10 described above in connection with FIGS. 1, 2A and 2B and is adapted for use in sterilization processes that utilize, among other agents, hydrogen-peroxide gas plasma as the sterilizing agent.

With reference to FIG. 3, trayliner 50 generally comprises a sheet of material 10 cut to substantially cover a base 52 of a sterilization tray 54. The base 52 of the sterilization tray 54 may be solid or perforated, as is known in the art. As shown, trayliner 50 is of rectangular configuration; however, alternative geometries are contemplated, e.g., as may be appropriate for specific sterilization tray configurations. Trayliners may be dimensioned depending upon the application. Preferred trayliners 50 measure approximately 12×12, 12×14, 12×16, 12×18, 12×20 and 12×22 inches, respectively, and are approximately ¼ inch in thickness. Trayliners 50 preferred for use in separating basins measure approximately 3×24 inches and may also be ¼ inch in thickness.

The trayliner 50 of the present invention may be used in a hydrogen-peroxide gas plasma sterilization system, an ethylene oxide sterilization system, or in other types of sterilization systems, either now known or later developed. As is known, a sterilization system generally includes a sterilization chamber that is adapted to receive instruments to be sterilized, and a source of a sterilizing agent, e.g., hydrogen-peroxide gas plasma, ethylene oxide, etc., connected to the sterilization chamber.

A preferred method for sterilizing surgical instruments 56 according to the present invention includes positioning the trayliner 50 in the base of the tray 54, as shown in FIGS. 3 and 4, and positioning instruments 56 on the trayliner 50. The types of instruments 56 that may benefit from the sterilization method disclosed herein includes all conventional surgical instruments, particularly reusable surgical instruments composed of stainless steel. Determinations as to the types of surgical instruments 56 to be placed on tray 54, the numbers/weights of such surgical instruments, the spacing of such surgical instruments, sterilization cycles, and the like, are made according to conventional sterilization criteria. Although not shown, a trayliner 50 could also be placed on top of the instruments, as will be apparent to persons skilled in the art.

As shown in the alternative embodiment of FIG. 4, tray 54 contains trayliner 50 and a plurality of instruments 56 positioned thereon. Tray 54 is then wrapped in a sterilization wrap 58 fabricated from a material compatible with the sterilization process being employed and, optionally, a second trayliner 50 or other cushioning member may be placed between tray 54 and sterilization wrap 58, thereby reducing the risk that wrap 58 may be damaged by the corners of tray 54. Once wrapped in the sterilization wrap 58, tray 54 is ready to be placed in a sterilization unit for sterilization of surgical instruments 56. At the conclusion of the sterilization cycle, tray 54 is typically removed from the sterilization unit (not pictured), and the sterilized instruments 56 are, in due course, removed from the tray and made ready for subsequent surgical procedures. At the conclusion of the sterilization cycle, the trayliner 50 of the present invention is typically disposed of in a conventional waste container.

The present invention, therefore, provides a trayliner 50 that functions to cushion surgical instruments in connection with the sterilization process, while at the same time not interfering with the sterilization process (e.g., by not disadvantageously absorbing hydrogen peroxide vapors so as to reduce the amount of plasma generated). The trayliner 50 permits proper sterilant penetration/evacuation, and delivery of sterilized surgical instruments substantially at the conclusion of a sterilization process. The trayliner 50 also permits effective aeration of instruments.

Figure 5:
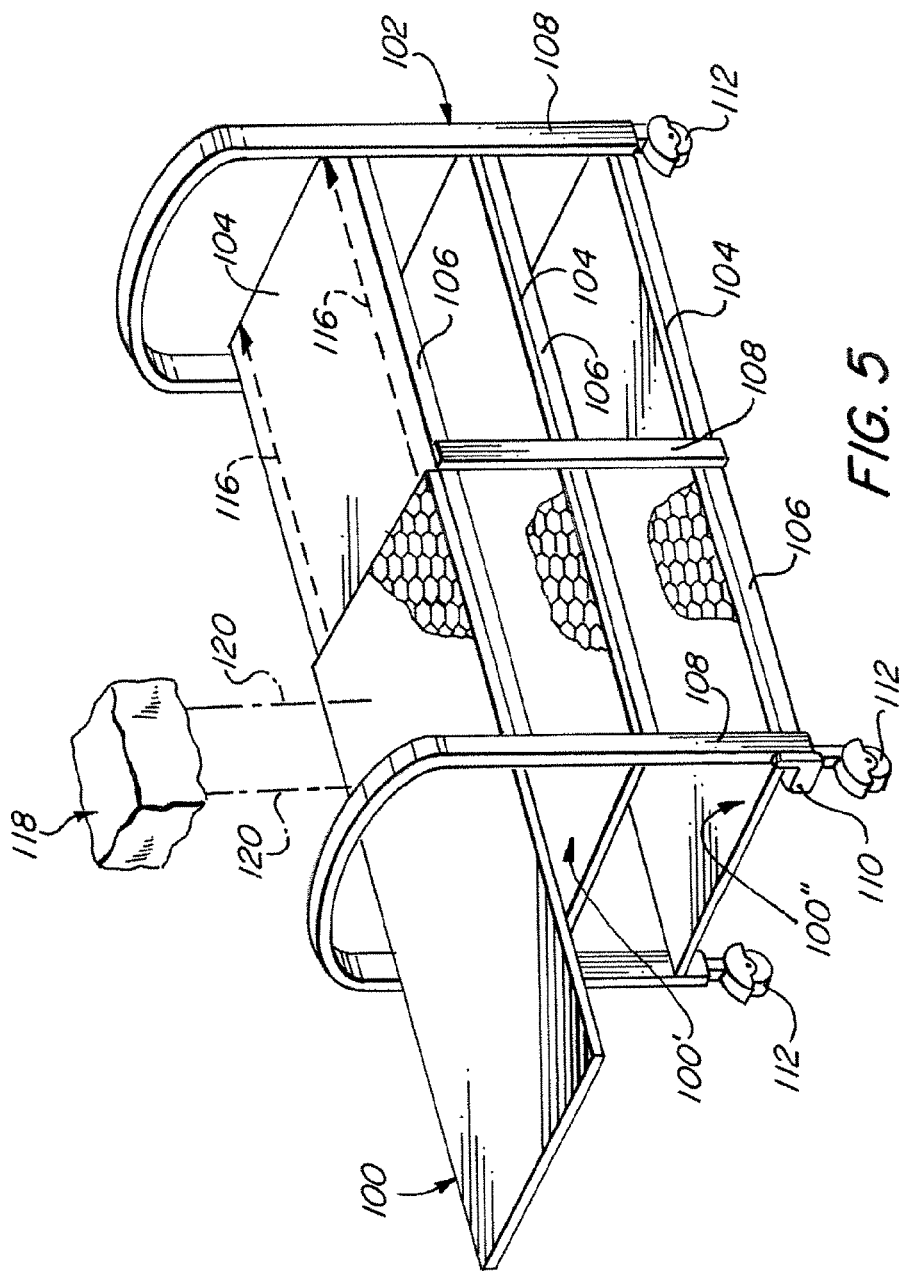
FIG. 5 is a perspective view of a sterilization cart including two fully mounted shelf-liners and one partially mounted shelf-liner that are formed from the open cellular material of FIG. 1.

Another embodiment of a sterilization accessory in accordance with the present invention is illustrated in FIG. 5. In particular, shelf-liners 100, 100' and 100" are provided, each of which is composed of the open cellular material 10 described above in connection with FIGS. 1, 2A and 2B. In addition, each of the shelf-liners 100, 100' and 100" are dimensioned for use with a sterilization carriage or cart such as that shown at 102. As shown, the sterilization cart 102 is generally composed of steel and includes sheet-like shelves 104 which are supported by horizontal beams 106 and vertical posts 108 having flanges 110. Casters 112 also may be provided for ease in movement of the sterilization cart 102. It will be appreciated that the sterilization cart 102 may be used in conjunction with, or loaded onto, other sterilization carts as is well known to the skilled artisan. One particular sterilization cart useful in the practice of the present invention is sold by the STERIS® corporation of Mentor, Ohio, under the mark AMSCO®.

The shelf-liners 100' and 100" are illustrated as being mounted on a shelf 104 and shelf-liner 100 is illustrated as being partially mounted requiring movement in the direction of arrows 114 for completing the mounting thereof. Once the shelf-liner 100 is mounted, the loading of, for example, a sterilization pack such as a wrapped tray 118 may be carried out in the direction of arrows 120.

It will be appreciated that each of the shelf-liners 100, 100' and 100" may be dimensioned in accordance with the size of the sterilization cart. Preferred shelf-liners 100, 100' and 100" measure approximately 22×48 and 22×60 inches, respectively, and are approximately ¼ inch in thickness. Shelf-liners of such dimensions should stand up to multiple sterilization cycles before requiring replacement. However, it will be understood that over-loading, otherwise improper loading of the sterilization cart or improper operation of the sterilizer may significantly reduce the number of sterilization cycles that the shelf-liner may withstand.

Figure 6:
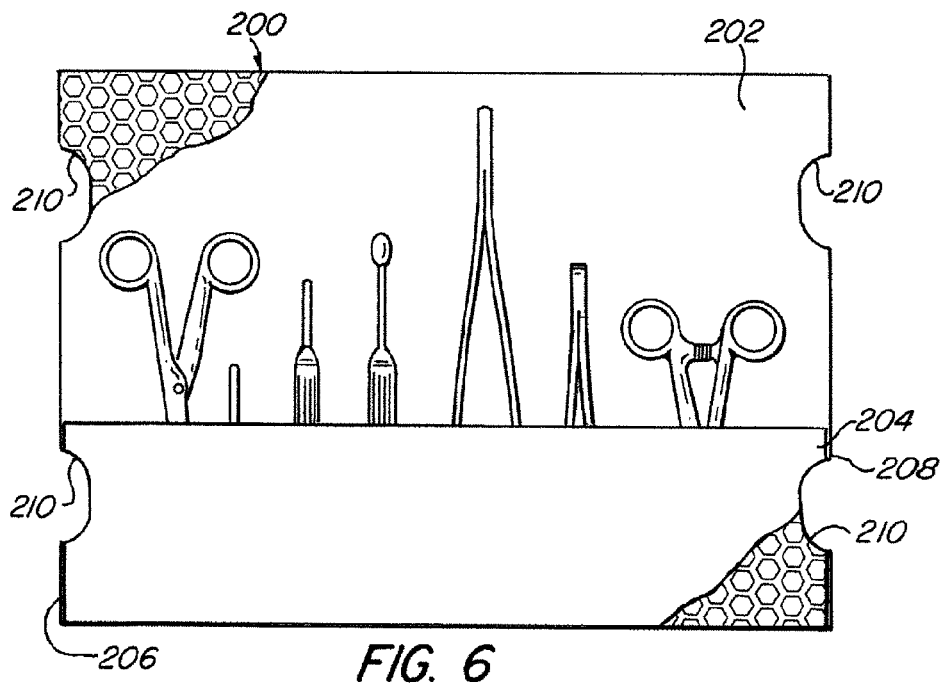
FIG. 6 is a front view of an instrument pouch formed from the open cellular material of FIG. 1, containing miscellaneous surgical instruments.

An instrument pouch 200 for containing an article in the tray 54 of a sterilization unit, such as a hydrogen-peroxide gas plasma sterilization unit, such that the article is cushioned, is also provided by the present disclosure, as shown in FIG. 6. The instrument pouch 200 is made of the open cellular material 10 described above in connection with FIGS. 1, 2A and 2B, and includes a backing sheet 202 for cushioning the article. The sheet 202 is preferably provided in substantially the same size and shape as the base 52 of the tray 54. A pocket 204 is secured to the sheet 202 such that at least a portion of an article to be sterilized can be received between the pocket 204 and the sheet 202. Preferably, the pocket 204 is unitary with the backing sheet 202 and folded over the backing sheet, with side edges 206, 208 of the pocket being secured to the backing sheet. The side edges 206, 208 are preferably secured to the backing sheet 202 by heating and applying pressure such that the side edges are bonded to the backing sheet 202. Thus, the instrument pouch 200 includes a single large pocket 204, which can contain a plurality of articles, such as surgical instruments like scissors, tweezers and scalpels. Articles that have been sterilized within the instrument pouch 200, can be left in the instrument pouch, after the sterilization process, until the sterilized article is actually used. Then, the instrument pouch 200 is preferably disposed of.

The open cellular nature of material 10 from which pouch 200 is made allows the sterilizing agent, such as hydrogen-peroxide vapor and plasma, to pass through the tray and the instrument pouch to sterilize the article, and also allows the sterilizing agent, such as liquid hydrogen-peroxide, to drain from the tray. The instrument pouch 200 may include notches 210 corresponding to channels (not shown) provided in the sidewall of some trays, as is known in the art.

Figure 7:
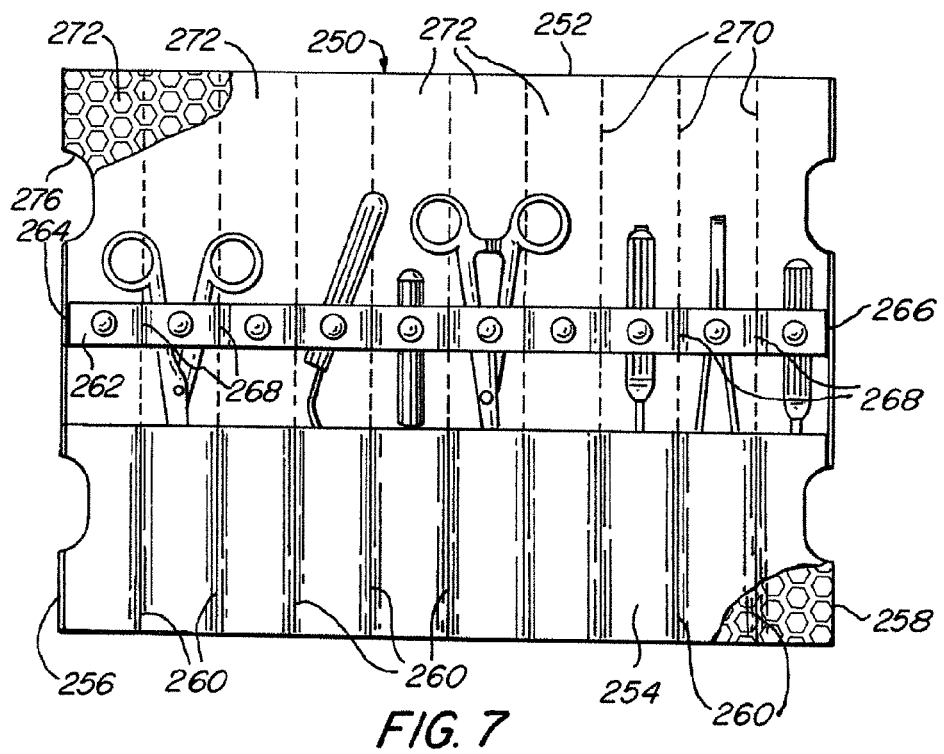
FIG. 7 is a front view of a sheet of individually-severeable instrument pouches formed from the open cellular material of FIG. 1, containing miscellaneous surgical instruments.

Another instrument pouch 250 formed from the open cellular material 10 described above in connection with FIGS. 1, 2A and 2B is shown in FIG. 7. The instrument pouch 250 includes a backing sheet 252, preferably provided in substantially the same size and shape as the base 52 of the tray 54, and a pocket 254 secured to the sheet. The pocket 254 is unitary with the backing sheet 252 and folded over the backing sheet, with side edges 256, 258 of the pocket being secured to the backing sheet. The pocket 254 is also secured to the sheet at equally spaced-apart intervals 260 parallel with and between the side edges 256, 258. Thus, the instrument pouch 250 includes a plurality of small pockets, each for containing a single article, as shown. The pouch 250 also includes strip 262, also preferably formed from the open cellular material 10, secured to the backing sheet 252 and spaced from the pocket 254. The strip 262 is secured at its ends 264, 266 and at equally spaced intervals 268 between the ends, such that it acts as a belt for securing the articles. The instrument pouch 250 can also include perforations 270 aligned with the intervals 268 of the strip 262 and the intervals 260 of the pocket 254, such that individual article pouches 272 can be torn from the larger instrument pouch 250. The instrument pouch 250 may also has a multiplicity of notches 276 similar the pouch 200 of FIG. 6.

FIGS. 8A-8D show various instrument pouches 280, 282, 284, 286 formed from the open cellular material 10 described above in connection with FIGS. 1, 2A and 2B according to the present disclosure, with each pouch holding an article, such as an ophthalmic device 278. Each instrument pouch includes a backing sheet 288. The instrument pouch 280 of FIG. 8A simply includes a relatively large pocket 290, while the instrument pouch 282 of FIG. 8B includes a relatively smaller pocket 292 and a belt 294 spaced from the pocket. The belt 294 is formed from a strip of open cellular material 10 secured to the backing sheet 288. The instrument pouch 284 of FIG. 8C includes a pocket 296 and a belt 298 spaced from the pocket. The belt 298 is formed from two parallel spaced slits 300, 302 provided in the backing sheet 288. The instrument pouch 286 of FIG. 8D includes pockets 304, 306 secured to both ends of the backing sheet 288. Thus, instrument pouches according to the present invention can be provided in various shapes, sizes and configurations.

The present invention, therefore, provides a sterilization accessory which is formed of a material that is capable of being used in conjunction with hydrogen-peroxide gas plasma sterilization, which is formed of a material that does not undesirably trap significant amounts of hydrogen peroxide therein so as to reduce the effectiveness of the sterilization operation, which is formed of a material that does not undesirably chemically react with hydrogen peroxide so as to reduce the effectiveness of the sterilization operation, and which is relatively inexpensive to produce, thereby making it cost effective to dispose of each accessory after a single use.

Although the invention has been described with reference to a particular arrangement of parts, features and the like, these are not intended to exhaust all possible arrangements or features, and indeed many other modifications and variations will be ascertainable to those of skill in the art.

What is claimed is:

1. A sterilization system for sterilizing a surgical instrument, said sterilization system comprising:
   a generally planar sterilization surface; and
   a sterilization accessory disposed on said generally planar sterilization surface that receives the surgical instrument thereon or therein, said sterilization accessory consisting essentially of a single sheet of material shaped such that it comprises:
      a generally planar base surface;
      a plurality of cells extending from said base surface, each of said plurality of cells comprising a side wall, which extends from said base surface, and an end wall at least a portion of which is disposed generally parallel to the base surface, said side wall and said end wall together defining a cell volume;
   wherein each of said plurality of cells has formed in the end wall or the side wall thereof, an aperture, which aperture permits gases surrounding the single sheet of material to pass into and out of each of said plurality of cells; and
   wherein each of the end walls of the plurality of cells comprises an exterior surface and the surgical instrument is received on the exterior surfaces of the end walls.

2. The sterilization system of claim 1 wherein the side wall of each of said plurality of cells extends from said base surface at an angle oblique with respect thereto.

3. The sterilization system of claim 1 wherein the end wall is discrete from the side wall of each of said plurality of cells, such that a clear demarcation therebetween is readily ascertainable.

4. The sterilization system of claim 1 wherein the end wall is integrally formed with the side wall of each of said plurality of cells, such that a clear demarcation therebetween is not readily ascertainable.

5. The sterilization system of claim 1 wherein each of said plurality of cells has a hexagonal cross section.

6. The sterilization system of claim 1 wherein said generally planar sterilization surface comprises a sterilization tray.

7. The sterilization system of claim 1 wherein said generally planar sterilization surface comprises a shelf of a sterilization cart.

8. The sterilization system of claim 1 wherein said sterilization accessory forms a trayliner or shelf liner.

9. The sterilization system of claim 1 wherein said sterilization accessory forms an instrument pouch.

10. The sterilization system of claim 1, wherein the sheet of material is olefin-based.

11. The sterilization system of claim 10 wherein the sheet of material comprises at least one of polyethylene and polypropylene.

* * * * *